(12) United States Patent
Perko

(10) Patent No.: US 9,913,740 B2
(45) Date of Patent: Mar. 13, 2018

(54) STENT WITH VARYING CROSS-SECTION

(71) Applicant: W. L. Gore & Associates, Inc., Newark, DE (US)

(72) Inventor: Vincent L. Perko, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 91 days.

(21) Appl. No.: 14/047,599

(22) Filed: Oct. 7, 2013

(65) Prior Publication Data

US 2014/0121756 A1 May 1, 2014

Related U.S. Application Data

(60) Provisional application No. 61/718,500, filed on Oct. 25, 2012.

(51) Int. Cl.
| | | |
|---|---|---|
| *A61F 2/915* | (2013.01) | |
| *A61F 2/07* | (2013.01) | |
| *B21F 5/00* | (2006.01) | |
| *B21F 45/00* | (2006.01) | |

(52) U.S. Cl.
CPC ............ *A61F 2/915* (2013.01); *A61F 2/07* (2013.01); *B21F 5/00* (2013.01); *B21F 45/008* (2013.01); *A61F 2220/005* (2013.01); *A61F 2220/0041* (2013.01); *A61F 2220/0075* (2013.01); *A61F 2230/0013* (2013.01); *A61F 2250/002* (2013.01); *A61F 2250/0014* (2013.01); *A61F 2250/0018* (2013.01); *A61F 2250/0036* (2013.01); *Y10T 29/49* (2015.01)

(58) Field of Classification Search
None
See application file for complete search history.

(56) References Cited

U.S. PATENT DOCUMENTS

| | | | |
|---|---|---|---|
| 2,867,807 A | | 1/1959 | Anstett |
| 3,868,956 A | | 3/1975 | Alfidi et al. |
| 4,886,062 A | * | 12/1989 | Wiktor ............ A61F 2/88 267/180 |
| 5,575,816 A | * | 11/1996 | Rudnick ............ B21F 45/008 623/1.15 |
| 6,309,414 B1 | * | 10/2001 | Rolando ............ A61F 2/91 623/1.15 |
| 6,719,782 B1 | | 4/2004 | Chuter |
| 7,344,563 B2 | | 3/2008 | Vallana et al. |
| 7,500,376 B2 | | 3/2009 | Bathurst et al. |
| 7,651,523 B2 | | 1/2010 | Eller |
| 7,740,653 B1 | | 6/2010 | Pollock et al. |
| 7,857,842 B2 | | 12/2010 | Chuter |

(Continued)

FOREIGN PATENT DOCUMENTS

| | | |
|---|---|---|
| CN | 101426454 A | 5/2009 |
| CN | 102711677 A | 10/2012 |

(Continued)

OTHER PUBLICATIONS

International Search Report for PCT/US2013/063862 dated Dec. 5, 2013 corresponding to U.S. Appl. No. 14/047,599, 6 pages.

*Primary Examiner* — Leslie Lopez

(57) ABSTRACT

The present disclosure describes methods and apparatus for endoluminal devices, such as stents, that have components with varying cross-sections at various points about the length of the endoluminal device, with various benefits resulting therefrom.

32 Claims, 6 Drawing Sheets

(56) References Cited

U.S. PATENT DOCUMENTS

| | | |
|---|---|---|
| 8,024,851 B2 | 9/2011 | Barr et al. |
| 8,585,753 B2 | 11/2013 | Scanlon |
| 2003/0045898 A1 | 3/2003 | Harrision et al. |
| 2003/0105511 A1* | 6/2003 | Welsh ............... A61F 2/915 623/1.15 |
| 2004/0106978 A1 | 6/2004 | Greenberg |
| 2006/0224234 A1 | 10/2006 | Jayaraman |
| 2008/0177376 A1* | 7/2008 | Krivoruchko ............. A61F 2/90 623/1.16 |
| 2011/0071619 A1* | 3/2011 | Bliss .................... A61F 2/88 623/1.16 |
| 2011/0112626 A1* | 5/2011 | van der Leest ........... A61F 2/91 623/1.15 |
| 2012/0029619 A1 | 2/2012 | Schroeder |

FOREIGN PATENT DOCUMENTS

| | | |
|---|---|---|
| EP | 0 806 190 | 11/1997 |
| EP | 1 066 804 | 1/2001 |
| EP | 0 888 093 | 7/2001 |
| JP | 2002-530146 | 9/2002 |
| JP | 2008-546452 | 12/2008 |
| JP | 2010-501274 A | 1/2010 |
| JP | 2010-269161 | 12/2010 |
| WO | 88/07774 | 10/1988 |
| WO | WO-2000/030563 | 6/2000 |
| WO | 02/13725 | 2/2002 |
| WO | 2006/138548 | 12/2006 |
| WO | WO-2006138548 A | 12/2006 |
| WO | WO-2008/024712 A2 | 2/2008 |
| WO | 2011/042810 | 4/2011 |

\* cited by examiner

STENT WITH VARYING CROSS-SECTION

FIELD

The present disclosure relates generally to endoluminal devices and, more specifically, to endoluminal devices such as stents that have components with varying cross-sections.

BACKGROUND

Endoluminal devices such as stents, grafts, filters, valves, anchors, occluders, and other implantable devices are frequently used to treat the vasculature of human patients. Such devices often include a frame comprising a stent which may be used alone or in connection with other materials such as graft or filtering materials. It may be desirable that the stent have varying levels of flexibility in different directions of motion and/or a lower profile, at various points along its length. Thus, there is a need for stents that provide such characteristics.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

DETAILED DESCRIPTION OF THE ILLUSTRATED EMBODIMENTS

Figure 1A:
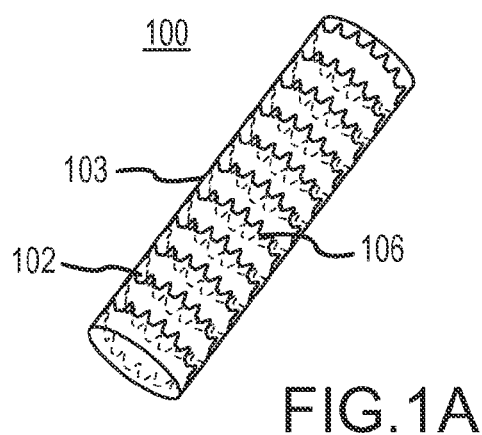
FIG. 1A illustrates a perspective view of helical stent.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure can be described in connection with various principles and beliefs, the present disclosure should not be bound by theory.

Endoluminal or implantable devices such as stents, grafts, filters, valves, anchors, occluders, and other implantable devices are frequently used to treat the vasculature of human patients. These treatments or procedures are commonly referred to as intraluminal or endovascular procedures. Such endoluminal devices, including stents and stent-grafts, are generally tube like structures that define a lumen inserted into the vasculature to open and/or maintain the vasculature in order to prevent or address localized flow constriction, weakening of the vasculature wall, aneurysms, etc.

Figure 1B:
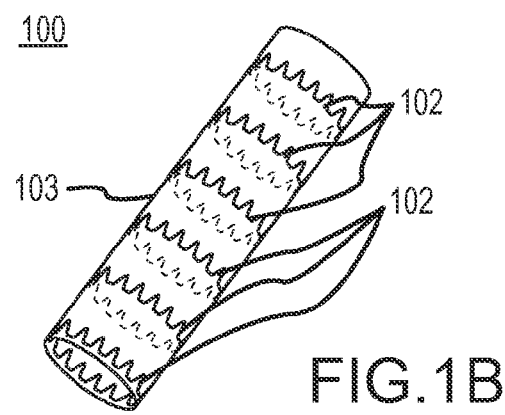
FIG. 1B illustrates a perspective view of stent comprised of a plurality of rings.

For example, in some embodiments, a stent 100 such as illustrated in FIG. 1A or 1B, comprises one or more wires 102 which can be used alone or in connection with various graft or filtering materials 103 now known or as yet unknown. For example, such graft or filtering materials 103 can comprise any number of biocompatible materials, such as, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof.

In various embodiments, the stent 100 can comprise a wire 102 with a "helical" configuration and can include various further patterns along its length such as an undulating pattern with angular apical areas 106 interconnected by generally straight sections 116 (FIG. 1A). In another embodiment, the stent 100 can comprise one or more rings of wire 102 (FIG. 1B). In various embodiments, the stent 100 has dimensions appropriate for the desired vascular treatment and with sufficient strength to provide structural support for the flexible wall of the endoluminal device and/or the vasculature.

Briefly, as used herein, "wire" or "wires" (e.g., wire 102) refers to a member or strand which, if oriented along a line, has a relatively long length in relation to the breadth of its cross-section, such as an extruded strand of metal or polymer (as noted below), and which can be wound into a particular pattern or shape. A "wire" or "wires" can also refer to a member or strand which is cut from a larger piece of material, such as a tube or planar sheet of material. In various embodiments, the wire can be hollow or otherwise contain various cavities therein along a portion or the entirety of its length.

Additionally, as used herein, a "cross-section" of a wire refers to a section of the wire formed by a plane cutting through the wire at right angle to its axis at a particular location (or along a portion of the wire proximate the location), such as at a first location, second location, third location and so on. Thus, one wire can have numerous distinct cross-sections (which can have the same or different shapes) at various locations or along various portions along its length.

In various embodiments, among other configurations, the wire(s) 102 can be helical and, optionally, have sinusoidal or zig-zag patterns such as an undulating pattern with angular apical areas interconnected by generally straight sections 116 as illustrated in FIG. 1A. In other embodiments, the wire(s) 102 can be helical, but linear (without any undulations), or as shown in FIG. 1B, can be comprised of individual rings. In various embodiments, stent 100 can be formed from a length of wire such as, but not limited to, an extruded wire, or can be cut from a tube. In any case, whether or not wound or cut, the resulting stent 100 can have any size, shape, or pattern suitable for a vascular treatment.

In some embodiments, the stent 100 is comprised of a shape-memory material, such as, but not limited to, nitinol. In other embodiments, however, the stent 100 can be comprised of other materials, self-expandable or otherwise expandable (e.g., with a balloon or spring mechanism), such as various metals (e.g., stainless steel), alloys and polymers.

In various embodiments, the materials and components of the stents, grafts, filters, valves, anchors, occluders, and other implantable devices in accordance with the present disclosure can also include one or more bioactive agents. For example, the materials or components can be coated by a therapeutic agent such as, for example, heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, thalidomide, and many others.

Figure 2:
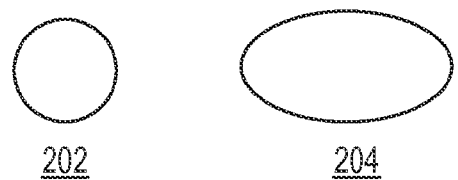
FIG. 2 illustrates various elliptical cross-sectional shapes.

In accordance with the present disclosure, the wire 102 comprises a cross-section 104. Cross-section 104 can be of any shape, such as but not limited to, elliptical or non-elliptical. In this regard, as used herein, an "elliptical" shape refers to any shape that generally lacks a point where two lines, curves, or surfaces converge to form an angle. For example, with reference to FIG. 2, an "elliptical" shape encompasses traditional Euclidian geometric shapes such as circles 202 and ellipses 204, as well as other non-angular shapes 206 (that lack any angles), even if those shapes do not have designations common in Euclidian geometry.

Figure 3:
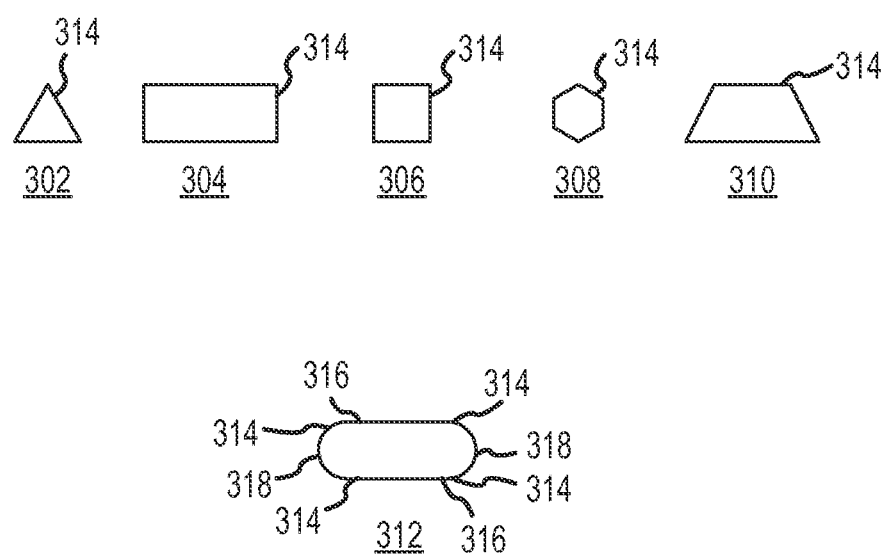
FIG. 3 illustrates various non-elliptical cross-sectional shapes.

As used herein, a "non-elliptical" shape refers to any shape that includes at least one point where two lines, curves, or surfaces converge to form an angle. For example, with reference to FIG. 3, a "non-elliptical" shape encompasses traditional Euclidian geometric shapes such as triangles 302, rectangles 304, squares 306, hexagons 308, trapezoids 310, and the like as well as other shapes that have at least one angle 314 even if those shapes do not have designations common in Euclidian geometry. By way of example, an atypical shape 312 defined by two parallel lines 316 connected by two polynomial curves 318, while appearing generally "smooth," nonetheless has four angles 314 and is thus non-elliptical.

In some embodiments, it can be desirable for the stent 100 to have varying levels of flexibility in different directions of motion and at various points along its length for purposes of, for example, collapsing and expanding the stent 100 and/or to facilitate desired bending of the stent about its axis. In this regard, as may be used herein, "flexibility" refers to the physical characteristic of the ability of a material allow bending without unduly damaging or fatiguing the material.

In contrast to "flexibility," as may be used herein, the physical characteristic of "stiffness" generally has a contrary meaning. Namely, "stiffness" refers to the characteristic of resistance to bending or the characteristic of being more rigid. Thus, increased flexibility refers to an increased ability to allow bending without damaging the material, while increased stiffness refers to an increased resistance to bending without damaging the material.

In this regard, many intraluminal and endovascular procedures using endoluminal devices such as stent 100 provide advantages over surgery, such that when intraluminal or endovascular treatment is an option, it is often the more desirable option. This desire arises from the fact that such procedures tend to be a more minimally invasive method of treating diseases than surgical methods. Benefits of minimally invasive procedures include more rapid procedures, shorter hospital stays, quicker recoveries, and lower risk of complications.

However, to expand the number of procedures that may be performed intraluminally or endovascularly, improvements in the ability to deliver and deploy an endoluminal device from a remote location, typically a location outside the body, are beneficial. For example, to improve delivery, smaller delivery profiles, namely, the diameter of the endoluminal device inserted, are desirable to help traverse irregularly shaped, tortuous, heavily branched, or narrow lumens or vessels to gain access to the treatment site. For these and other reasons, endoluminal devices with improved flexibility in various directions and at various points on the endoluminal device are desirable.

Thus, in an embodiment, different portions of the stent 100 (e.g., first portion, second portion, third portion, etc.) can have shapes that vary, change or are otherwise altered in such a manner as to lower the profile and/or change the flexibility of the stent 100 along those portions. For example, in an embodiment, the flexibility of the stent 100 in a particular direction along a portion having one cross-section 104' may be affected so that it differs from the flexibility in the same direction along another portion of the same stent 100 having a differently shaped cross-section 104. As will be described in more detail below, these changes in shape include varying the shape of the cross-section 104' from one shape exhibiting one flexibility to a different shape which exhibits a different flexibility. For example, in an embodiment, a change of shape in the cross-section 104' in accordance with the present disclosure includes a change in the cross-section 104' from a generally elliptical shape to a generally non-elliptical shape. In an embodiment and as described in more detail, such a change can comprise flattening the cross-section 104' proximate a particular location. In various embodiments, though the shape of cross-section 104' can be changed, the area of cross-section 104' is generally changed only nominally, if at all, because, in such embodiments, material is not necessarily removed, but rather redistributed.

Figure 4B:
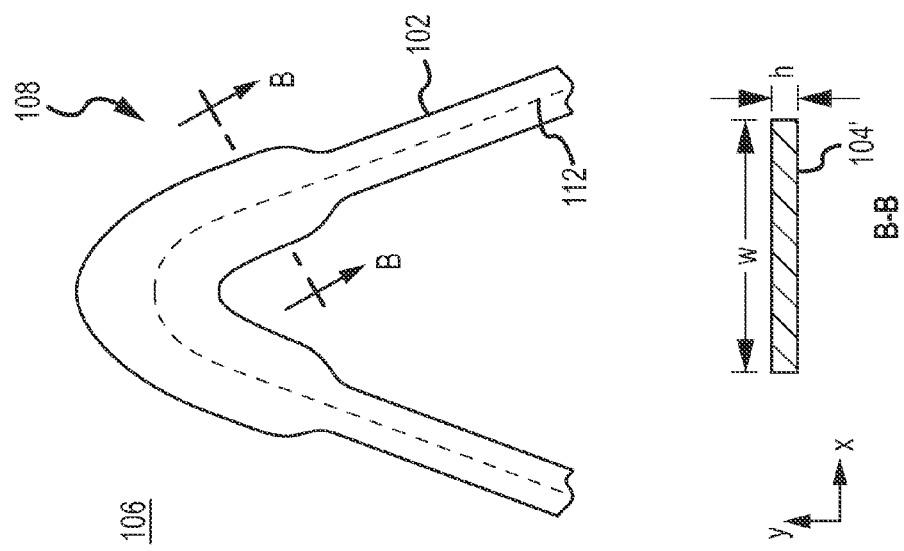
FIG. 4B illustrates a close-up view of an apical area of a stent and a cross-sectional view of the same after the cross-sectional shape has been changed from the cross-sectional shape of FIG. 4A.
Figure 4A:
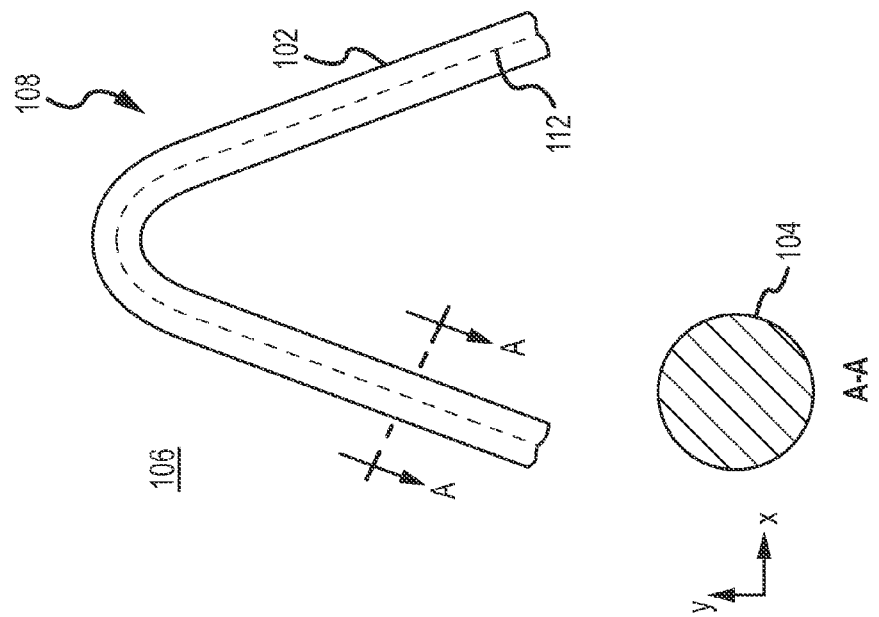
FIG. 4A illustrates a close-up view of an apical area of a stent and a cross-sectional view of the same.

For example, with reference to FIG. 4A, a close-up view of an apical area 106 of FIG. 1A illustrates the wire 102 of one apex 108 of a helically wound, undulating stent 100 formed by winding a nitinol wire in a helically wound, undulating form. Alternatively, in other embodiments, the stent 100 can be cut from a nitinol tube. In either case, the close-up of FIG. 4A illustrates the apical area 106 prior to any change in the shape of the cross-section 104. In this regard, with reference to section A-A, an elliptical shape is shown. In this illustrated embodiment, the elliptical cross-section 104 is a circle, though in other embodiments the wire 102 can have other generally elliptical shapes as defined above prior to the change noted above. In FIG. 4A, prior to any change, this elliptical shape is generally continuous through apical area 106.

In contrast, with reference to FIG. 4B, a close-up view of the same apical area 106 of FIG. 1A illustrates the wire 102 of the apex 108 after changing the shape of the cross-section 104. With specific reference to section B-B in FIG. 4B, a non-elliptical shape is shown. In this illustrated embodiment, the non-elliptical cross-section 104 is has been flattened from the previous generally elliptical shape to a generally rectangular shape, though in other embodiments the wire 102 can have other generally non-elliptical shapes as defined above.

By changing the shape of the cross-section 104 from a generally elliptical to a generally non-elliptical shape, the flexibility is changed along the axes of cross-section 104. Stated another way, the stiffness of the cross-section 104 is changed along the opposite axes of cross-section 104. The change in flexibility (or stiffness) can be attributed to a change in what is known as the "moment of inertia of a plane area" or the "second area moment" of the cross-section 104. The moment of inertia of a plane area is a property of the cross-section 104 that can be used to determine the resistance of the wire 102 to bending about an axis 112 of the wire 102. For example, such determinations can be accomplished by finite element methods or similar mathematical computations.

Thus, with reference to an embodiment such as illustrated in FIGS. 4A and 4B, section A-A has been flattened from a generally elliptical shape in FIG. 4A to a generally non-elliptical shape in section B-B of FIG. 4B, thereby changing the flexibility of the wire 102 in apical area 106. Specifically, about the x-axis of section B-B of the flattened (non-elliptical) wire 102, the wire 102 exhibits less flexibility than exhibited about the x-axis of section A-A of the unflattened (elliptical) wire 102. Stated otherwise, about the x-axis of section B-B of the flattened (non-elliptical) wire 102, the wire 102 exhibits a greater stiffness than about the x-axis of section A-A of the unflattened (elliptical) wire 102.

In contrast, with continued reference to FIGS. 4A and 4B and sections A-A and B-B, about the y-axis of section B-B of the flattened (non-elliptical) wire 102, the wire 102 will exhibit more flexibility than about the y-axis of section A-A of the unflattened (elliptical) wire 102. Stated otherwise, about the y-axis of section B-B of the flattened (non-elliptical) wire 102, the wire 102 exhibits a smaller stiffness than about the y-axis of section A-A of the unflattened (elliptical) wire 102.

Thus, by changing the cross-section 104 of the wire 102, for example, in apical areas 106, the flexibility/stiffness can be changed or optimized. Benefits of changes in flexibility or stiffness include reduced stresses and strains in the wire 102 due to bending during insertion and traversal of the vasculature, or collapsing and expansion of the stent 100 during loading and deployment of the endoluminal device. Other benefits can include the normalization of stresses and strains along the stent 100, which can in turn lower the profile of the stent 100 and increase the fatigue life of the stent 100.

In various embodiments, changing the shape of the cross-section 104 from generally elliptical to generally non-elliptical can be accomplished by various operations. For example, in some embodiments, this flattening can be done by "coining" the wire 102 at desired locations using various presses, forging machinery, clamps or the like. Similarly, other machining operations such as milling, cutting (mechanical, plasma, laser, or the like) can used, and in still others, various casting, molding or extruding techniques can be used to change the cross-section 104 of the wire 102. For example, in an embodiment where the stent 100 is formed on a mandrel, a press or clamp could compress the wire 102 at desired locations to flatten it. Alternatively, the stent 100 can be unwound/removed from the mandrel and the flattening operations could be applied at that time to the desired locations.

Figure 8:
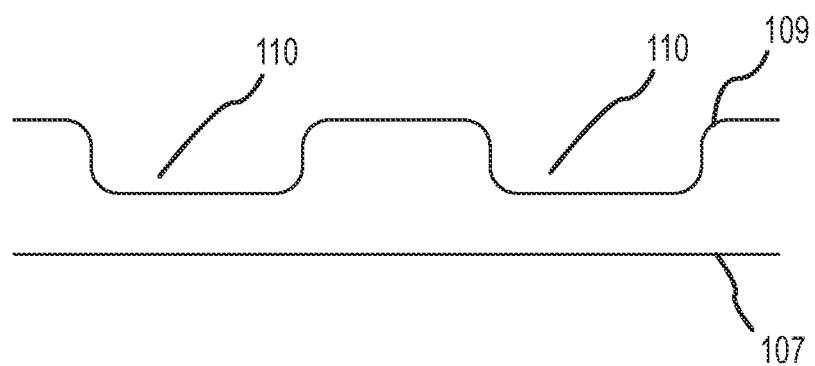
FIG. 8 is a partial cross sectional view of a wire for forming a stent having a substantially continuous side and an opposite, substantially opposite non-continuous side.

In embodiments such as those described herein, the profile of the wire 102 can beneficially have a substantially continuous side 107 (or "flat") and a substantially non-continuous side 109 (or "patterned"), for example, as illustrated in FIG. 8. Additionally, in some embodiments, the flattening of various portions of the wire 102 can be facilitated by using hollow wire in those portions.

With reference to FIG. 4B and section B-B for example, in some embodiments, by flattening various cross-sections 104 of the wire 102 to non-elliptical shapes, a flattened region 110 is created, which in turn, can provide a longer width (w) along the x-axis and thus an expanded surface area proximate flattened region 110. This expanded surface area of flattened region 110 along the x-axis can provide additional benefits such as an increase in attachment points for other materials such as, but not limited to, graft materials, filters or the like.

In some embodiments, when flattened regions 110 are created, a reduced height (h) surface area along the y-axis at that location results. The reduced height of the flattened region 110 along the y-axis can provide additional benefits such as a lower height profile, which can be useful when inserting an endoluminal device during endovascular procedures.

Figure 5:
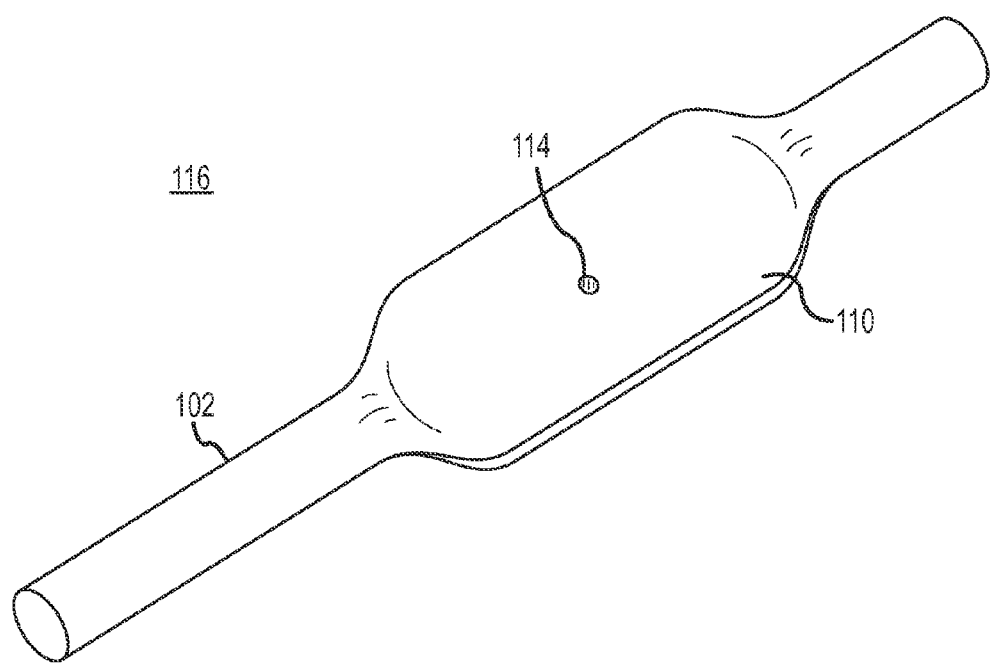
FIG. 5 illustrates a perspective view of a straight section of a stent.

Additionally, with reference now to FIG. 5 for example, in some embodiments, the flattened region 110 (or portion with a generally non-elliptical cross-section) can be formed in the wire 102 in other portions of the wire 102, such as along a straight section 116 (instead of or in addition to the apical areas 106), thus exhibiting benefits similar to those described above. Additionally, different combinations of straight sections 116 and apical areas 106 can be flattened or left unflattened (non-elliptical or elliptical) depending on the characteristics such as flexibility desired the stent 100. For example, in one embodiment, it may be desirable to flatten every other straight section 116 and/or apical area 106. Alternatively, it may be desirable to flatten only one or the other of the straight sections 116 or the apical areas 106. Still further, any number of other combinations of flattened portions of the wire 102 of stent 100 fall within the scope of the present disclosure.

In various embodiments, the various flattened regions of the wire 102, such as, for example, flattened region 110 or apex 108 can further comprise an aperture 114 or a plurality thereof. The aperture 114 can comprise any type of hole through the flattened region and can facilitate attachment of materials such as grafts and filters by, for example, sutures, adhesives, rivets or other attachment mechanisms. Additionally, in some embodiments the aperture 114 can function as visual indicator of, for example, location of the flattened region, and potentially the endoluminal device itself. In this regard, the material of the wire 102 surrounding the aperture 114 can be radiopaque, but the lack of the radiopaque material in the aperture 114 provides a marker that can be viewed by X-rays and the like for assisting in locating and positioning of the endoluminal device.

Figure 6:
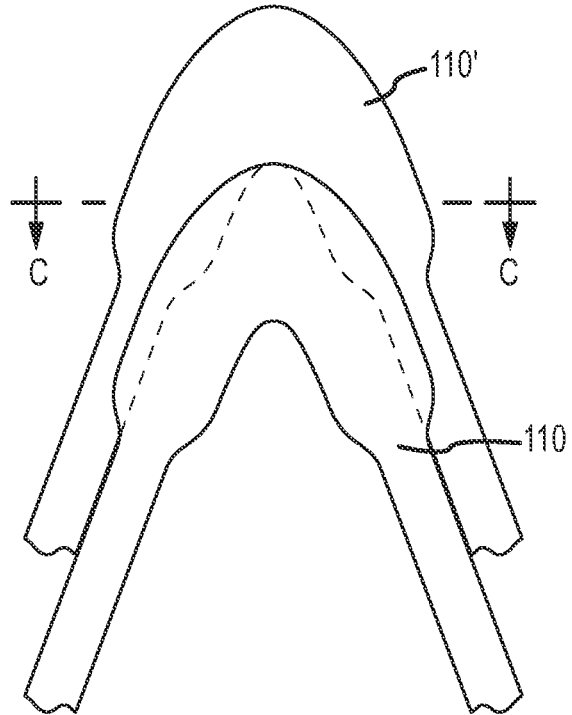
FIG. 6 illustrates a close-up view of two overlapping apical areas of a stent and a cross-sectional view of the same.
Figure 6:
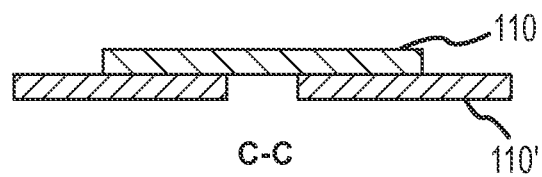
Figure 7:
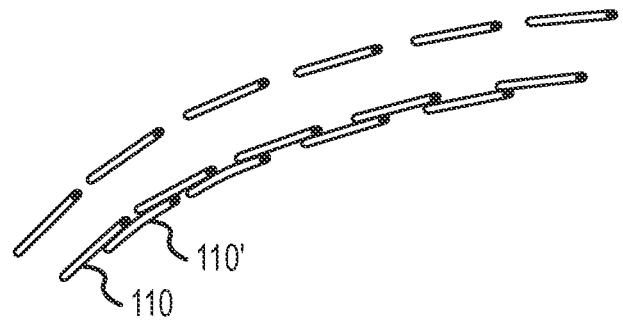
FIG. 7 illustrates a cross-sectional view a stent bending with overlapping apical areas.

As noted above, in some embodiments, the endoluminal devices can be collapsed, for example, to facilitate delivery to a vascular treatment site. As also noted above, varying degrees of flexibility of the collapsed endoluminal device may be desirable to assist the endoluminal device as it traverses the vasculature. As such, in some embodiments, it may be desirable for multiple flattened regions 110 of the wire 102 to be in proximity to one another when the endoluminal device is in a collapsed state. For example, with reference to FIG. 6, a close-up view of the flattened regions 110, 110' of two apical areas 106 of the wire 102 is shown. Section C-C illustrates the flattened region 110 above the flattened region 110'. As shown, the flattened region 110 is adjacent to and overlaps the flattened region 110', which, with reference to FIG. 7, can in turn facilitate the flattened regions 110, 110' sliding over one another as necessary as the collapsed endoluminal device bends during travel through the vasculature to a treatment site.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A method of forming a stent comprising:
   supplying a wire having a generally elliptical cross-section;
   changing a first portion of the wire to form a non-elliptical cross-section; and
   forming the wire into a generally tubular shaped stent by forming the wire into one or more coils including an undulating pattern with a series of apical areas interconnected by generally straight sections,
   wherein the generally tubular shaped stent comprises at least one annular portion, wherein, within the annular portion, the non-elliptical cross-section is located in the series of apical areas of the undulating pattern,
   wherein each apical area of the series of apical areas is not abutting end to end any other apical areas of the series of apical areas of adjacent coils of the tubular shaped stent in a final implanted configuration,
   wherein the series of apical areas extend at least one circumferential turn of the one or more coils, and
   wherein, within the annular portion, each generally straight section of the wire located between the apical areas of the series of apical areas of the undulating pattern comprises the generally elliptical cross-section.

2. The method of claim 1, wherein the generally elliptical cross-section is circular.

3. The method of claim 1, further comprising attaching a graft material to the non-elliptical cross-section.

4. The method of claim 1, further comprising forming an aperture in the non-elliptical cross-section.

5. The method of claim 1, wherein the non-elliptical cross-section is a flattened form of the generally elliptical cross-section.

6. The method of claim 5, wherein the non-elliptical cross-section is rectangular.

7. The method of claim 1, wherein forming the wire into the generally tubular shaped stent comprises winding the wire into a generally tubular form.

8. The method of claim 1, wherein forming the wire into the generally tubular shaped stent includes forming the wire into the generally tubular shaped stent on a mandrel.

9. The method of claim 1, wherein the non-elliptical cross-section is a first non-elliptical cross-section, the method further comprising forming a pattern on a first side of the wire, the pattern including a plurality of non-elliptical cross-sections on the first side of the wire, wherein forming the pattern includes changing the first portion of the wire to form the non-elliptical cross-section such that the plurality of non-elliptical cross-sections includes the first non-elliptical cross-section.

10. The method of claim 1, wherein the non-elliptical cross-section is a first non-elliptical cross-section, the method further comprising forming a pattern on the wire, the pattern including a plurality of non-elliptical cross-sections, wherein forming the pattern includes changing the first portion of the wire to form the non-elliptical cross-section such that the plurality of non-elliptical cross-sections includes the first non-elliptical cross-section.

11. The method of claim 10, wherein the plurality of non-elliptical cross-sections are located in the apical areas of the series of apical areas and separated by the generally elliptical cross-section.

12. The method of claim 11, wherein the generally elliptical cross-sections are located in the generally straight sections.

13. The method of claim 10, wherein the apical areas of the series of apical areas of the undulating pattern correspond to the plurality of non-elliptical cross-sections.

14. The method of claim 1, wherein apical areas of the series of apical areas of adjacent coils are oriented in a common direction.

15. The method of claim 1, wherein the stent is configured to allow the non-elliptical cross-sections of apical areas of the series of apical areas of adjacent coils to slide over one another when the stent bends while in a collapsed configuration.

16. The method of claim 1, wherein forming the wire into the one or more coils includes forming the wire into a helical configuration.

17. The method of claim 1, wherein forming the wire into the one or more coils includes forming the wire into individual rings.

18. A method of forming a stent comprising:
    supplying a wire having a generally elliptical cross-section;
    changing a first portion of the wire to form a pattern on the wire, the pattern including non-elliptical cross-sections separated by the generally elliptical cross-section; and
    forming the wire into a generally tubular shaped stent by forming the wire into one or more coils including an undulating pattern comprising a series of apical areas interconnected by generally straight sections, each apical area of the series of apical areas including one of the non-elliptical cross-sections, and each apical area of the series of apical areas being separated from adjacent apical areas of the series of apical areas by the generally elliptical cross-section,
    wherein each apical area of the series of apical areas is not abutting end to end any other apical areas of the series of apical areas of adjacent coils of the tubular shaped stent in a final implanted configuration, and
    wherein the series of apical areas extend at least one circumferential turn of the one or more coils.

19. The method of claim 18, wherein the generally elliptical cross-section is circular.

20. The method of claim 18, wherein the non-elliptical cross-sections are rectangular.

21. The method of claim 18, further comprising attaching a graft material to at least one of the non-elliptical cross-sections.

22. The method of claim 18, further comprising forming an aperture in at least one of the non-elliptical cross-sections.

23. The method of claim 18, wherein the non-elliptical cross-sections are a flattened form of the generally elliptical cross-section.

24. The method of claim 18, wherein forming the wire into the generally tubular shaped stent comprises winding the wire into a generally tubular form.

25. The method of claim 18, wherein forming the wire into the generally tubular shaped stent includes forming the wire into the generally tubular shaped stent on a mandrel.

26. The method of claim 18, wherein the non-elliptical cross-sections are on a first side of the wire.

27. The method of claim 18, wherein the generally elliptical cross-section is located in the generally straight sections.

28. The method of claim 18, wherein the series of apical areas interconnected by generally straight sections is within an annular portion of the generally tubular shaped stent.

29. The method of claim 18, wherein apical areas of the series of apical areas of adjacent coils are oriented in a common direction.

30. The method of claim 18, wherein the stent is configured to allow the non-elliptical cross-sections of apical areas of the series of apical areas of adjacent coils to slide over one another when the stent bends while in a collapsed configuration.

31. The method of claim 18, wherein forming the wire into the one or more coils includes forming the wire into a helical configuration.

32. The method of claim 18, wherein forming the wire into the one or more coils includes forming the wire into individual rings.

\* \* \* \* \*